United States Patent [19]

Dröge

[11] Patent Number: 5,744,157

[45] Date of Patent: Apr. 28, 1998

[54] PREPARATION FOR MAINTAINING AND/OR INCREASING MUSCULAR POWER AND BODY CELL MASS

[75] Inventor: Wulf Dröge, Heidelberg, Germany

[73] Assignee: The German Cancer Research Institute, Heidelberg, Germany

[21] Appl. No.: 367,332

[22] PCT Filed: Aug. 31, 1993

[86] PCT No.: PCT/EP93/02354

§ 371 Date: Sep. 1, 1995

§ 102(e) Date: Sep. 1, 1995

[87] PCT Pub. No.: WO94/05270

PCT Pub. Date: Mar. 17, 1994

[30] Foreign Application Priority Data

Sep. 1, 1992 [DE] Germany .................. 42 29 166.6

[51] Int. Cl.⁶ .................. A61K 9/127; A61K 47/42
[52] U.S. Cl. .................. 424/450; 424/439
[58] Field of Search .................. 424/439, 450

[56] References Cited

U.S. PATENT DOCUMENTS 5,292,773  3/1994  Hirsch et al. .................. 514/554

*Primary Examiner*—Carlos Azpuru
*Attorney, Agent, or Firm*—Pennie & Edmonds LLP

[57] ABSTRACT

The present invention relates to a preparation for maintaining and/or increasing muscular power and body cell mass, which contains a thiol compound, particularly cysteine, a derivative and/or analogue thereof as well as conventional excipients.

15 Claims, 1 Drawing Sheet

PREPARATION FOR MAINTAINING AND/OR INCREASING MUSCULAR POWER AND BODY CELL MASS

The present invention relates to a preparation for maintaining and/or increasing muscular power and body cell mass. The preparation contains a thiol compound, particularly cysteine, a derivative and/or analogue thereof as well as conventional excipients.

The muscular mass of a body influences not only its muscular power but also the entire protein metabolism of the body. The heavy loss of muscular mass and the accompanying reduction of the body cell mass and the most important amino acid reservoir of the body are frequent and life-threatening complications in the case of carcinoses and infectious diseases, such as the immunological deficiency AIDS. Furthermore, a progressive loss of skeletal muscular mass is found in patients suffering from non-insulinogenic diabetes (type 2 diabetes) as well as in the case of amyotrophic lateral sclerosis. When persons get older, they also undergo a progressive loss of skeletal muscular mass and muscular power. This is accompanied by diverse and constantly increasing symptoms which cover the wide range from muscle strains, impairments of the vertebral column to physical decline resulting from old age and acute need of care. The patients generally feel the cachectic processes to be especially burdening. There is no satisfactory treatment for this by now. Also in the case of slighter muscular troubles such as lumbago, overstretching and accompanying secondary complaints such as backache and impairments of the vertebral column, it has not yet been possible to correct satisfactorily one of the most important causes of these problems, namely the progressive loss of muscular cell mass and muscular power, respectively.

Thus, the object of the present invention is to provide a preparation with which the above-mentioned problems can be treated successfully.

According to the invention this is achieved by providing a preparation which contains a thiol compound, particularly cysteine, a derivative and/or analogue thereof as well as conventional excipients. Glutathione is also to be counted among the favorable thiol compounds. N-acetylcysteine and homocysteine as well as a thiazolidine derivative of cysteine, e.g. 2-oxo-4-thiazolidine carboxylate, are also to be mentioned as being especially suitable.

In a preferred embodiment the preparation according to the invention includes a substance which improves the absorption of the active compound(s) by the cell. It is possible to use conventional substances for this purpose, which facilitate the substance transport into the cells. It is preferred to use liposomes, into the lumina of which the active compound(s) are incorporated. Liposomes are produced according to usual processes described in the literature.

In another preferred embodiment the preparation according to the invention includes a substance which increases the effectiveness of active compound(s). Such a substance is e.g. a hormone such as insulin or insulin-like growth factor, a vitamin, a nutrient such as glucose, or an amino acid, or a conventional, sarcoplastic drug such as an anabolic steroid.

The preparation according to the invention usefully contains 5–95, preferably 30–70, and in particular 40–60, % by weight of active compound or active compounds, and 95–5, preferably 70–30, and in particular 60–30, % by weight of conventional excipients. The preparation can be applied in the usual ways e.g. orally, parenterally or locally, the oral application being preferred. Furthermore, the preparation can be applied in conventional forms e.g. as a solution, suspension, emulsion, powder, tablet, capsule or ointment, with enteric-coated capsules being preferred. In addition, the excipients used may be the conventional ones such as drug carriers, binders, blasting agents, lubricating agents, solvents, solutizers, release accelerators, release retarders, emulsifiers, stabilizers (e.g. antioxidants, buffers), coloring agents or taste improvers. The solvent preferred is pyrogen-free water or physiological saline solution, a concentration of $10^{-5}$ to $10^{-1}$ preferably $10^{-3}$ to $10^{-2}$ g, of active compound(s) per liter offering itself.

The dosage of the preparation according to the invention ranges usefully from 50 mg–5 g, preferably 200 mg–4 g, and is in particular 2×200 mg, of active compound(s) daily. However, in the individual case a dosage differing therefrom may be necessary and easily be determined by a person skilled in the art.

The preparation according to the invention renders possible to maintain and/or increase the muscular power and body cell mass of a human or animal body, irrespective of whether it is ill or healthy. This preparation is suitable to treat cachectic processes occurring as a complication in connection with carcinoses and infectious diseases such as AIDS but also at an advanced age. It can also be used in the case of muscular injuries such as overstretching and rupture. Furthermore, reference has to be made to its possible use in healthy persons. In this case, it serves for obtaining a strengthening of the muscular mass and thus an increased efficiency.

The following examples serve for explaining the invention.

EXAMPLE 1

Effect of N-acetylcysteine on the Efficiency of a Test Person

A man who has run a defined distance of about 9 km in hilly terrain in the course of his regular leisure-time sport almost regularly once a week for over 10 years, has a performance decline caused by his age between the age of 45 and 50, which is accompanied by a deterioration of the period needed from about 52 to 55 minutes to 65 to 70 minutes. After regular administration of N-acetylcysteine (2×200 mg daily), the time needed for said distances was reduced to 47.5 minutes within 8 weeks and otherwise constant program of physical exercise. The period needed for the defined, steeply rising stage was improved from about 10.5 minutes to 7.5 minutes within the same period of time.

EXAMPLE 2

Effect of N-acetylcysteine on the Lactate Values of Test Persons

N-acetylcysteine was administered to 13 healthy male persons between the age of 20 and 60 years in a dosage of 2×200 mg 3 times a week over a period of 4 weeks. The study was randomized and carried out in a double-blind trial with an equal number of placebo-treated control persons.

During this 4-week period, the probands performed a comprehensive program of physical exercise with a defined, substantially anaerobic training particularly of the arm muscles. The muscle strength and the locally venous lactate concentration in the cubital vein, among other things, were measured at various times after the termination of a standardized muscle training (handgrip tests) (Sinkeler et al., Muscle & Nerve (1985), pages 523 to 527). In this connection, the decrease of the lactate concentration after the training served as a measure of the aerobic capacity of the strained muscles.

Figure 1:
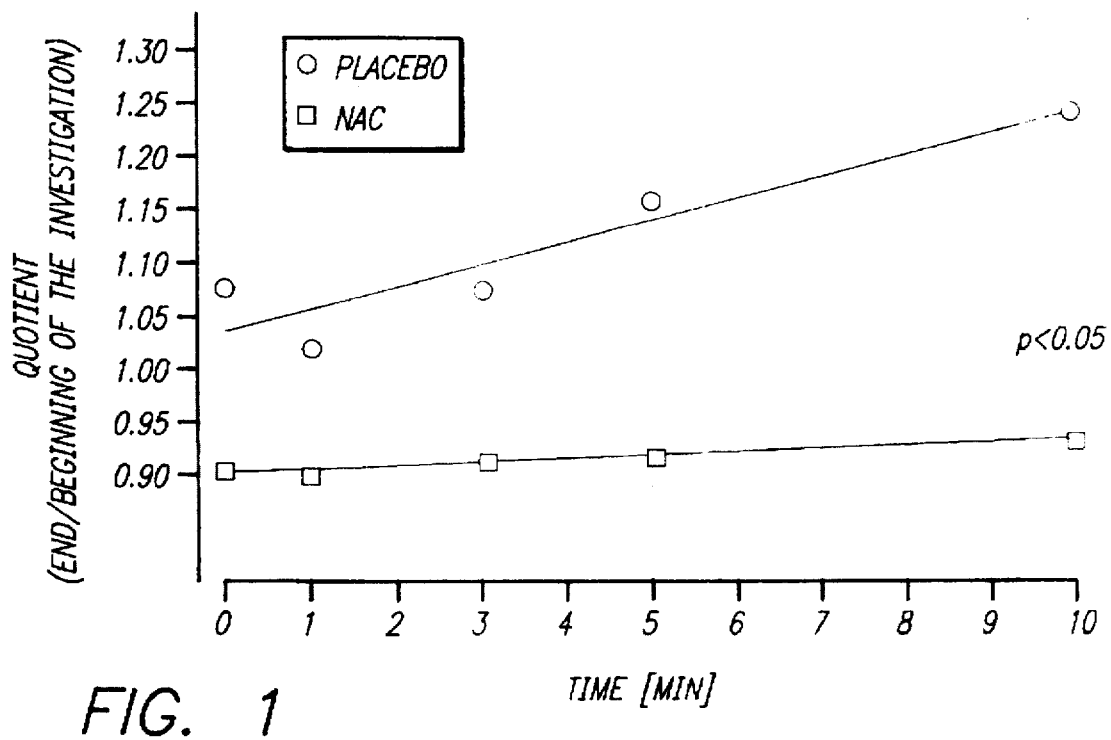
FIG. 1. Relation of lactate values at the beginning and the end of the investigation determined for various times after the strain.

The results in FIG. 1 show the quotients of the lactate values at the end of the study as compared to the corresponding lactate values at the beginning of the study. These quotients are a measure of the change in the aerobic efficiency during the 4-week anaerobic training program, i.e. a quotient of over 1 represents a deterioration of the aerobic efficiency. The results of this study show that the muscular force of both the test group and the placebo-treated group slightly improved on the average owing to the training program (data not shown). However, the aerobic capacity of the placebo-treated group deteriorated markedly, since the lactate values obtained 10 minutes after the strain were markedly higher at the end of the 4-week study than at the beginning of the study. The recovery of the muscles from the strongly glycolytic condition was thus worse at the end of the study than at the beginning of the study. The muscle training of the untreated standard persons was correspondingly not only accompanied by the positive effect of increase in muscular force resulting from the training but also by the negative effects on certain biochemical performances of the muscles. This deterioration could not be observed in persons treated with N-acetylcysteine (NAC).

EXAMPLE 3

Effect of Cysteine on the Cachectic Process of Tumor-bearing Mice

Figure 2:
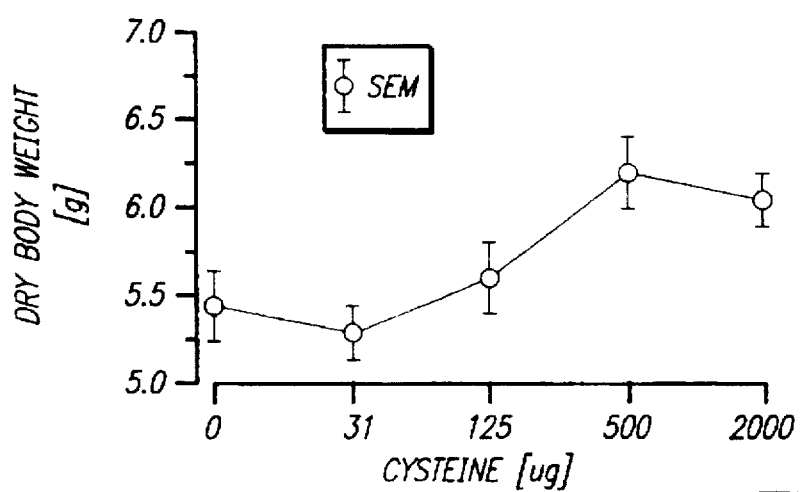
FIG. 2. Effect of cysteine on the dry body weight of female C57BL/6 mice having 24-day-old MCA105 tumors.

Syngeneic female C57BL/6 mice (8 to 12 weeks old) were inoculated with cells of the methylcholanthrene-induced MCA-105 fibrosarcoma. Each mouse received $3 \times 10^6$ MAC-105 cells subcutaneously. Groups of 6 tumor-bearing mice each received additionally intraperitoneal injections of cysteine of predetermined increasing concentrations on the same day and 5 succeeding days. 24 days after the tumor inoculation the mice were killed, the tumor was removed and the dry body weight of the mice was determined according to the method by Strassmann et al. (J. Clin. Invest. (1992) 89:1681–1684). The dry body weight of the tumor-free control mice was 7.1 g. The results of the investigation (FIG. 2) show that without cysteine the tumor-bearing mice had a dry body weight of about 5.5 g and correspondingly showed a strong cachexia. This cachexia was markedly reduced in a dose-dependent manner by cysteine.

EXAMPLE 4

Effect of N-acetylcysteine on the Body Cell Mass and Body Fat Mass in Healthy Human Persons Having Above Median Plasma-triglyceride and Plasma Glutamate Levels AIDS patients and cachectic cancer patients frequently have elevated plasma triglyceride and plasma glutamate levels. Healthy persons also show such symptoms occasionally. In this case, they reveal episodes with a relatively strong decrease in body cell mass and simultaneous building-up of body fat. This follows from recent studies conducted by the applicant.

N-acetylcysteine was administered to 17 healthy male persons of the above disposition—age between 20 and 60—for 4 weeks at doses of 2×200 mg 3 times a week. The study was randomized and carried out in a double-blind fashion with a corresponding number of placebo-treated control persons (n=21).

During these 4 weeks, the persons performed an extensive program of physical exercise with a defined, essentially anaerobic training, particularly of the arm muscles. The plasma triglyceride and plasma glutamate levels were evaluated before the commencement of the 4-week treatment period as well as after the conclusion thereof. Body cell mass and body fat portions were also determined before and after the 4-week treatment period by means of the known impedance analysis described in the literature. Body cell mass and body fat were calculated on the basis of body weight and data from the impedance analysis with the help of a computer program.

In the table, the results of this study reveal that the subjects showed indeed a significant decrease of the body cell mass by about 3.7% on the average within a relatively short period of time, which decrease is accompanied by a simultaneous marked increase in the amount of body fat. Since the body cell mass accounts for about 40 to 50% of the body weight and the body fat portion accounts for about 15 to 20% of the body weight in these subjects, the loss of body cell mass is fully compensated by the weight gain caused by the increase in body fat. In contrast to this loss of body cell mass in the placebo-treated control persons, the body cell mass in the corresponding N-acetylcysteine-treated persons was increased by 1.65%. In this case, the amount of body fat remained virtually unchanged. The differences between the N-acetylcysteine-treated and placebo-treated persons is in either case statistically significant by the Wilcoxon rank test.

Table

Effect of N-acetylcysteine on the body cell mass and body fat mass in healthy persons with relatively high plasma triglyceride and plasma glutamate levels

|  | placebo | +NAC | significance (Wilcoxon rank test) |
|---|---|---|---|
| % change of the body cell mass | −3.73 ± 1.21 | +1.65 ± 1.61 | P < 0.02 |
| % change of the body fat mass | +10.74 ± 2.60 | −0.04 ± 1.25 | P < 0.02 |

I claim:

1. A method for maintaining and/or increasing muscular power and body cell mass in a subject, comprising administering a pharmaceutical formulation having a thiol as an active compound wherein the formulation contains about 5 to about 95% by weight of the active compound in an acceptable pharmaceutical carrier to the subject.

2. The method of claim 1, wherein the subject has a disease selected from the group consisting of cachetic carcinosis, type 2 diabetes, amyotrophic lateral sclerosis, atrophy of body cell mass, and reduced muscular power resulting from old age.

3. A method for reducing the amount of body fat of a subject, comprising administering a pharmaceutical formulation having a thiol as an active compound wherein the formulation contains 5 to 95% by weight of the active compound in an acceptable pharmaceutical carrier to the subject.

4. The method of claim 3, wherein the subject has high plasma triglyceride and plasma glutamate levels which are above average.

5. The method of claim 1, wherein the active compound is selected from the group consisting of cysteine, N-acetylcysteine, homocysteine, a thiazolidine derivative of cysteine, and 2-oxo-4-thiazolidine carboxylate.

6. The method of claim 3, wherein the active compound is selected from the group consisting of cysteine, N-acetylcysteine, homocysteine, a thiazolidine derivative of cysteine, and 2-oxo-4-thiazolidine carboxylate.

7. The method of claim 1 or 3, wherein the active compound is cysteine.

8. The method of claim 1 or 3, wherein the active compound is N-acetylcysteine.

9. The method of claim 1 or 3, wherein the active compound is homocysteine.

10. The method of claim 1 or 3, wherein the active compound is a thiazolidine derivative of cysteine.

11. The method of claim 10, wherein the thiazolidine derivative is 2-oxo-4-thiazolidine carboxylate.

12. The method of claim 1 or 3, wherein the pharmaceutical preparation additionally contains a substance for improved cellular absorption of the active compound.

13. The method of claim 12, wherein the substance is a liposome.

14. The method of claim 1 or 5, wherein the pharmaceutical preparation contains an additional substance promoting the maintenance and/or increase of muscular power and body cell mass.

15. The method of claim 14, wherein the substance is selected from the group consisting of a hormone, vitamin, nutrient and a conventional muscle growth stimulating drug.

* * * * *

UNITED STATES PATENT AND TRADEMARK OFFICE
CERTIFICATE OF CORRECTION

PATENT NO. : 5,744,157
DATED : April 28, 1998
INVENTOR(S) : Wulf Dröge

It is certified that error appears in the above-identified patent and that said Letters Patent is hereby corrected as shown below:

On the front page, please change the Assignee [73] from "The German Cancer Research Institute, Heidelberg, Germany" to --Wulf Dröge, Heidelberg, Germany--.

Signed and Sealed this

Twenty-ninth Day of May, 2001

*Attest:*

NICHOLAS P. GODICI

*Attesting Officer*     *Acting Director of the United States Patent and Trademark Office*